(12) United States Patent
Kovarik et al.

(10) Patent No.: US 10,314,865 B2
(45) Date of Patent: *Jun. 11, 2019

(54) METHOD AND SYSTEM FOR TREATING CANCER AND OTHER AGE-RELATED DISEASES BY EXTENDING THE HEALTHSPAN OF A HUMAN

(71) Applicants: Katherine Rose Kovarik, Englewood, CO (US); Joseph E. Kovarik, Englewood, CO (US)

(72) Inventors: Katherine Rose Kovarik, Englewood, CO (US); Joseph E. Kovarik, Englewood, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/639,767

(22) Filed: Jun. 30, 2017

(65) Prior Publication Data
US 2017/0348359 A1 Dec. 7, 2017

Related U.S. Application Data

(63) Continuation-in-part of application No. 15/437,976, filed on Feb. 21, 2017, now Pat. No. 9,730,967, and a continuation-in-part of application No. 15/403,823, filed on Jan. 11, 2017, now Pat. No. 10,111,913, and a continuation-in-part of application No. 15/395,419, filed on Dec. 30, 2016, now Pat. No. 10,086,018, and a continuation-in-part of application No. 15/392,173, filed on Dec. 28, 2016, and a continuation-in-part of application No. 15/385,278, filed on Dec. 20, 2016, now Pat. No. 10,085,938, and a continuation-in-part of application No. 15/384,716, filed on Dec. 20, 2016, now Pat. No. 9,987,224, and a continuation-in-part of application No. 15/378,425, filed on Dec. 14, 2016, (Continued)

(51) Int. Cl.
| | |
|---|---|
| A61K 9/00 | (2006.01) |
| A61K 31/40 | (2006.01) |
| A61K 35/00 | (2006.01) |
| A61K 35/74 | (2015.01) |
| A61K 31/366 | (2006.01) |
| A61K 35/745 | (2015.01) |
| A61K 35/742 | (2015.01) |
| A61K 35/741 | (2015.01) |
| A61K 45/06 | (2006.01) |
| A61K 31/58 | (2006.01) |
| A61K 31/436 | (2006.01) |
| A61K 31/505 | (2006.01) |
| A61K 35/747 | (2015.01) |
| A61K 38/17 | (2006.01) |
| A61K 38/46 | (2006.01) |
| A61K 39/35 | (2006.01) |
| A61K 39/07 | (2006.01) |
| A61K 31/438 | (2006.01) |

(52) U.S. Cl.
CPC ............ *A61K 35/74* (2013.01); *A61K 9/0014* (2013.01); *A61K 9/0034* (2013.01); *A61K 9/0043* (2013.01); *A61K 9/0053* (2013.01); *A61K 31/366* (2013.01); *A61K 31/40* (2013.01); *A61K 31/436* (2013.01); *A61K 31/438* (2013.01); *A61K 31/505* (2013.01); *A61K 31/58* (2013.01); *A61K 35/741* (2013.01); *A61K 35/742* (2013.01); *A61K 35/745* (2013.01); *A61K 35/747* (2013.01); *A61K 38/1758* (2013.01); *A61K 38/465* (2013.01); *A61K 39/07* (2013.01); *A61K 39/35* (2013.01); *A61K 45/06* (2013.01); *C12Y 301/03048* (2013.01); *C12Y 301/03067* (2013.01); *A61K 2035/11* (2013.01)

(58) Field of Classification Search
None
See application file for complete search history.

(56) References Cited

U.S. PATENT DOCUMENTS

| | | |
|---|---|---|
| 3,178,341 A | 4/1965 | Hamill et al. |
| 4,568,639 A | 2/1986 | Lew |

(Continued)

FOREIGN PATENT DOCUMENTS

| | | |
|---|---|---|
| WO | WO 2011/020780 | 2/2011 |
| WO | WO 2013/026000 | 2/2013 |

(Continued)

OTHER PUBLICATIONS

Sporn et al., "Chemoprevention of Cancer," Carcinogenesis, vol. 21 (2000), 525-530.*
Auerbach et al. (Cancer and Metastasis Reviews, 2000, 19: 167-172).*
Gura (Science, 1997, 278(5340): 1041-1042.*
Jain RK (Scientific American, Jul. 1994,58-65).*
Hennessy et al., "Statins inhibit bacterial growth and virulence," Antimicrobial Agents and Chemotherapy accepted manuscript, 2016, downloaded from http://aac.asm.org, downloaded on Mar. 21, 2017, 46 pages.

(Continued)

*Primary Examiner* — Brian Gangle
(74) *Attorney, Agent, or Firm* — Sheridan Ross P.C.

(57) ABSTRACT

Various embodiments of the present invention are directed to the field of Oncology, and in particular, embodiments directed to a method of ameliorating, treating, or preventing a malignancy in a human subject wherein the steps of the method assist or boost the immune system in eradicating cancerous cells. Certain embodiments are directed to the field of human longevity and aging in a manner such that cancer is not contracted due to ameliorating, treating, or reducing aging by increasing the healthspan and lifespan of humans. In certain embodiments, administration of beneficial bacteria to an individual's microbiome that have been modified so as to produce effective amounts of desired compositions, compounds, agents, e.g. tomatidine, rapamycin, p53 protein, statins, etc., is employed to treat and prevent cancer and other age-related diseases.

14 Claims, 3 Drawing Sheets

Related U.S. Application Data and a continuation-in-part of application No. 15/342,642, filed on Nov. 3, 2016, now Pat. No. 10,010,568, said application No. 15/437,976 is a continuation-in-part of application No. 15/228,454, filed on Aug. 4, 2016, now Pat. No. 9,585,920, application No. 15/639,767, which is a continuation-in-part of application No. 15/200,210, filed on Jul. 1, 2016, now abandoned, said application No. 15/228,454 is a continuation-in-part of application No. 14/954,074, filed on Nov. 30, 2015, now Pat. No. 9,457,077, said application No. 15/378,425 is a continuation of application No. 14/752,192, filed on Jun. 26, 2015, now Pat. No. 9,549,842, said application No. 14/954,074 is a continuation-in-part of application No. 14/574,517, filed on Dec. 18, 2014, now Pat. No. 9,408,880, said application No. 15/200,210 is a continuation-in-part of application No. 14/283,459, filed on May 21, 2014, now Pat. No. 9,387,168, said application No. 14/752,192 is a continuation-in-part of application No. 14/225,503, filed on Mar. 26, 2014, now Pat. No. 9,445,936, which is a continuation of application No. 13/367,052, filed on Feb. 6, 2012, now Pat. No. 8,701,671.

(60) Provisional application No. 62/296,186, filed on Feb. 17, 2016, provisional application No. 62/275,341, filed on Jan. 6, 2016, provisional application No. 62/274,550, filed on Jan. 4, 2016, provisional application No. 62/387,405, filed on Dec. 24, 2015, provisional application No. 62/387,404, filed on Dec. 24, 2015, provisional application No. 62/260,906, filed on Nov. 30, 2015, provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013, provisional application No. 61/556,023, filed on Nov. 4, 2011, provisional application No. 61/439,652, filed on Feb. 4, 2011.

(56) References Cited

U.S. PATENT DOCUMENTS

| | | |
|---|---|---|
| 4,687,841 A | 8/1987 | Spilburg et al. |
| 4,720,486 A | 1/1988 | Spilburg et al. |
| 4,995,555 A | 2/1991 | Woodruff |
| 5,277,877 A | 1/1994 | Jeffrey et al. |
| 5,614,501 A | 3/1997 | Richards |
| 6,287,610 B1 | 9/2001 | Bowling et al. |
| 6,569,474 B2 | 5/2003 | Clayton et al. |
| 6,722,577 B2 | 4/2004 | Dobyns, III |
| 7,353,194 B1 | 4/2008 | Kerker et al. |
| 7,540,432 B2 | 6/2009 | Majerowski et al. |
| 7,862,808 B2 | 1/2011 | Isolauri et al. |
| 8,030,457 B2 | 10/2011 | Jackson et al. |
| 8,034,601 B2 | 10/2011 | Boileau et al. |
| 8,034,606 B2 | 10/2011 | Park et al. |
| 8,110,215 B2 | 2/2012 | Koenig et al. |
| 8,197,872 B2 | 6/2012 | Mills et al. |
| 8,349,313 B2 | 1/2013 | Smith et al. |
| 8,357,368 B2 | 1/2013 | Dudek et al. |
| 8,362,206 B2 | 1/2013 | Wallach et al. |
| 8,420,074 B2 | 4/2013 | Rehberger et al. |
| 8,454,729 B2 | 6/2013 | Mittelmark et al. |
| 8,496,914 B2 | 7/2013 | Bonfiglio |
| 8,585,588 B2 | 11/2013 | Kovarik et al. |
| 8,591,412 B2 | 11/2013 | Kovarik et al. |
| 8,701,671 B2 | 4/2014 | Kovarik |
| 8,829,165 B2 | 9/2014 | Jackson et al. |
| 8,859,741 B2 | 10/2014 | Jackson et al. |
| 8,945,839 B2 | 2/2015 | Zhang |
| 9,010,340 B2 | 4/2015 | Kovarik et al. |
| 9,011,834 B1 | 4/2015 | McKenzie et al. |
| 9,044,420 B2 | 6/2015 | Dubensky, Jr. et al. |
| 9,045,547 B2 | 6/2015 | Jackson et al. |
| 9,254,295 B2 | 2/2016 | Adams et al. |
| 9,295,682 B2 | 3/2016 | Nunes |
| 9,387,168 B2 | 7/2016 | Barreca et al. |
| 9,408,559 B2 | 8/2016 | Kovarik et al. |
| 9,408,880 B2 | 8/2016 | Kovarik et al. |
| 9,445,936 B2 | 9/2016 | Kovarik |
| 9,457,077 B2 | 10/2016 | Kovarik et al. |
| 9,549,842 B2 | 1/2017 | Kovarik |
| 9,585,920 B2 | 3/2017 | Kovarik et al. |
| 9,730,967 B2 | 8/2017 | Kovarik et al. |
| 9,750,802 B2 | 9/2017 | Kovarik et al. |
| 2003/0206995 A1 | 11/2003 | Bowling et al. |
| 2004/0053352 A1 | 3/2004 | Ouyang et al. |
| 2004/0115223 A1 | 6/2004 | Follansbee |
| 2004/0142463 A1 | 7/2004 | Walker et al. |
| 2004/0166501 A1 | 8/2004 | Azimzai et al. |
| 2005/0118655 A1 | 6/2005 | Weinstock et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0123448 A1 | 5/2007 | Kaplan et al. |
| 2007/0207955 A1 | 9/2007 | Tanihara et al. |
| 2007/0231923 A1 | 10/2007 | Cumberland et al. |
| 2008/0112983 A1 | 5/2008 | Bufe et al. |
| 2008/0305089 A1 | 12/2008 | Bufe et al. |
| 2009/0205083 A1 | 8/2009 | Gupta et al. |
| 2010/0029832 A1 | 2/2010 | Pinnavaia et al. |
| 2010/0260720 A1 | 10/2010 | Sprenger |
| 2012/0029832 A1 | 2/2012 | Dodgson |
| 2012/0039806 A1 | 2/2012 | Lahoud et al. |
| 2012/0128597 A1 | 5/2012 | Peters et al. |
| 2012/0142548 A1 | 6/2012 | Corsi et al. |
| 2012/0276143 A1 | 11/2012 | O'Mahony et al. |
| 2013/0059815 A1 | 3/2013 | Fournell et al. |
| 2013/0157876 A1 | 6/2013 | Lynch et al. |
| 2013/0225440 A1 | 8/2013 | Friedman et al. |
| 2013/0259834 A1 | 10/2013 | Klaenhammer et al. |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0030332 A1 | 1/2014 | Baron et al. |
| 2014/0044677 A1 | 2/2014 | Qvit-Raz et al. |
| 2014/0045744 A1 | 2/2014 | Gordon |
| 2014/0068797 A1 | 3/2014 | Doudna et al. |
| 2014/0154290 A1 | 6/2014 | Peters et al. |
| 2014/0255351 A1 | 9/2014 | Berstad et al. |
| 2014/0349405 A1 | 11/2014 | Sontheimer et al. |
| 2014/0363441 A1 | 12/2014 | Grandea, III et al. |
| 2014/0364460 A1 | 12/2014 | Freed-Pastor et al. |
| 2014/0377278 A1 | 12/2014 | Elinav et al. |
| 2015/0004130 A1 | 1/2015 | Faber et al. |
| 2015/0064138 A1 | 3/2015 | Lu et al. |
| 2015/0071957 A1 | 3/2015 | Kelly et al. |
| 2015/0086581 A1 | 3/2015 | Li et al. |
| 2015/0132263 A1 | 5/2015 | Liu et al. |
| 2015/0147371 A1 | 5/2015 | Kovarik et al. |
| 2015/0190435 A1 | 7/2015 | Henn et al. |
| 2015/0252358 A1 | 9/2015 | Maeder et al. |
| 2016/0000754 A1 | 1/2016 | Stamets |
| 2016/0000841 A1 | 1/2016 | Yamamoto et al. |
| 2016/0069921 A1 | 3/2016 | Holmes et al. |
| 2016/0095316 A1 | 4/2016 | Goodman et al. |
| 2016/0151428 A1 | 6/2016 | Bryan |
| 2016/0158294 A1 | 6/2016 | von Maltzahn et al. |
| 2016/0175327 A1 | 6/2016 | Adams et al. |
| 2016/0199424 A1 | 7/2016 | Berry et al. |

(56) References Cited

U.S. PATENT DOCUMENTS

| | | |
|---|---|---|
| 2016/0206666 A1 | 7/2016 | Falb et al. |
| 2016/0206668 A1 | 7/2016 | Kort et al. |
| 2016/0213702 A1 | 7/2016 | von Maltzahn et al. |
| 2016/0243132 A1 | 8/2016 | Adams et al. |
| 2016/0271106 A1 | 9/2016 | Shi et al. |
| 2016/0354416 A1 | 12/2016 | Gajewski et al. |
| 2016/0374941 A1 | 12/2016 | Barreca et al. |
| 2017/0020932 A1 | 1/2017 | Cutcliffe et al. |
| 2017/0042924 A1 | 2/2017 | Otsuka et al. |
| 2017/0071986 A1 | 3/2017 | Kovarik et al. |
| 2017/0100328 A1 | 4/2017 | Kovarik et al. |
| 2017/0100329 A1 | 4/2017 | Kovarik et al. |
| 2017/0100330 A1 | 4/2017 | Kovarik et al. |
| 2017/0106025 A1 | 4/2017 | Kovarik |
| 2017/0106026 A1 | 4/2017 | Kovarik |
| 2017/0119827 A1 | 5/2017 | Kovarik |

FOREIGN PATENT DOCUMENTS

| | | |
|---|---|---|
| WO | WO 2013/107750 | 7/2013 |
| WO | WO 2014/103488 | 7/2014 |
| WO | WO 2015/069682 | 5/2015 |

OTHER PUBLICATIONS

Kilkkinen et al., "Use of antimicrobials and risk of type 1 diabetes in a population-based mother-child cohort," Diabetologia, 2006, vol. 49, pp. 66-70.

Kimoto et al., "New Lactococcus Strain with Immunomodulatory Activity: Enhancement of Th1-Type Immune Response," Microbiol. Immunol., 2004, vol. 48(2), pp. 75-82.

Norton et al., "The immune response to Lactococcus lactis: Implications for its use as a vaccine delivery vehicle," FEMS Microbiology Letters, 1994, vol. 120(3), pp. 249-256, abstract only, 2 page.

Repa et al., "Mucosal co-application of lactic acid bacteria and allergen induces counter-regulatory immune responses in a murine model of birch pollen allergy," Vaccine, 2003, vol. 22(1), pp. 87-95, abstract only, 1 page.

Zhao et al., Microbiome-generated amyloid and potential impact on amyloidogenesis in Alzheimer's disease (AD), Journal of Nature and Science, 2015, vol. 1(7), pp. 1-5.

Official Action for U.S. Appl. No. 14/574,517, dated Jan. 6, 2016, 13 pages.

Notice of Allowance for U.S. Appl. No. 14/574,517, dated Apr. 15, 2016, 8 pages.

Official Action for U.S. Appl. No. 14/954,074, dated Jun. 30, 2016, 4 pages.

Notice of Allowance for U.S. Appl. No. 14/954,074, dated Jul. 20, 2016, 7 pages.

Official Action for U.S. Appl. No. 15/270,034, dated Apr. 6, 2017, 5 pages.

Notice of Allowance for U.S. Appl. No. 15/270,034, dated May 5, 2017 7 pages.

Official Action for U.S. Appl. No. 15/228,454, dated Sep. 23, 2016, 13 pages.

Notice of Allowance for U.S. Appl. No. 15/228,454, dated Jan. 23, 2017, 7 pages.

Official Action for U.S. Appl. No. 15/437,976, dated Mar. 29, 2017, 8 pages.

Notice of Allowance for U.S. Appl. No. 15/437,976, dated Jul. 12, 2017 7 pages.

\* cited by examiner methylene blue

Tomatidine

Metformin

METHOD AND SYSTEM FOR TREATING CANCER AND OTHER AGE-RELATED DISEASES BY EXTENDING THE HEALTHSPAN OF A HUMAN

RELATED APPLICATIONS

This application is a continuation-in-part application of U.S. patent application Ser. No. 15/437,976, filed Feb. 21, 2017, which is a continuation-in-part of U.S. patent application Ser. No. 15/228,454, filed Aug. 4, 2016 (now issued U.S. Pat. No. 9,585,920, issued Mar. 7, 2017), which is a continuation-in-part application of U.S. patent application Ser. No. 14/954,074, filed on Nov. 30, 2015 (now issued U.S. Pat. No. 9,457,077, issued Oct. 4, 2016), which is a continuation-in-part application of U.S. patent application Ser. No. 14/574,517, filed on Dec. 18, 2014 (now issued U.S. Pat. No. 9,408,880, issued Aug. 9, 2016), which is a non-provisional of U.S. Provisional Patent Application No. 62/072,476, filed on Oct. 30, 2014; U.S. Provisional Patent Application No. 62/053,926, filed on Sep. 23, 2014; U.S. Provisional Patent Application No. 62/014,855, filed on Jun. 20, 2014; and U.S. Provisional Application No. 61/919,297, filed on Dec. 20, 2013.

This application is a continuation-in-part application of U.S. patent application Ser. No. 15/403,823, filed Jan. 11, 2017, which is a non-provisional of U.S. Provisional Application No. 62/296,186, filed Feb. 17, 2016.

This application is a continuation-in-part application of U.S. patent application Ser. No. 15/392,173 filed Dec. 28, 2016, which is a non-provisional of U.S. Provisional Patent Application No. 62/275,341, filed Jan. 6, 2016.

This application is a continuation-in-part application of U.S. patent application Ser. No. 15/395,419, filed Dec. 30, 2016, which is a non-provisional of U.S. Provisional Patent No. 62/274,550 filed Jan. 4, 2016.

This application is a continuation-in-part application of U.S. patent application Ser. No. 15/342,642, filed Nov. 3, 2016, which is a non-provisional of U.S. Provisional Application No. 62/260,906 filed Nov. 30, 2015.

This application is a continuation-in-part application of U.S. patent application Ser. No. 15/200,210, filed Jul. 1, 2016, which is a continuation-in-part application of U.S. patent application Ser. No. 14/283,459, filed May 21, 2014 (now issued U.S. Pat. No. 9,387,168, issued Jul. 12, 2016).

This application is a continuation-in-part application of U.S. patent application Ser. No. 15/378,425, filed Dec. 14, 2016, which is a continuation of U.S. patent application Ser. No. 14/752,192, filed on Jun. 26, 2015 (now U.S. Pat. No. 9,549,842, issued Jan. 24, 2017), which is a continuation-in-part application of U.S. patent application Ser. No. 14/225,503, filed on Mar. 26, 2014 (now U.S. Pat. No. 9,445,936, issued Sep. 20, 2016), which is a continuation of U.S. patent application Ser. No. 13/367,052, filed Feb. 6, 2012 (now issued U.S. Pat. No. 8,701,671, issued Apr. 22, 2014), which is a non-provisional of U.S. Provisional Patent Application No. 61/556,023, filed on Nov. 4, 2011 and U.S. Provisional Patent Application No. 61/439,652, filed Feb. 4, 2011.

This application is a continuation-in-part application of U.S. patent application Ser. No. 15/385,278, filed Dec. 20, 2016, which is a non-provisional of U.S. Provisional Patent No. 62/387,404, filed Dec. 24, 2015.

This application is a continuation-in-part application of U.S. patent application Ser. No. 15/384,716, filed Dec. 20, 2016, which is a non-provisional of U.S. Provisional Patent No. 62/387,405, filed Dec. 24, 2015.

FIELD OF THE INVENTION

A method and system for treating and preventing cancer employing CRISPR-Cas technology to modify an individual's microbiome, and in particular to a method and system designed to produce tomatidine and/or rapamycin in an individual's microbiome in order to combat cancer. Various aspects of the present invention are directed to the long-sought and unsolved desire to extend human life and to develop a safe interventional strategy to delay aging and extend the healthspan of humans, thereby delaying the onset and incidence of cancer.

BACKGROUND OF THE INVENTION

Cancer causes millions of deaths a year worldwide and rates are also rising as more people live to an older age. It is anticipated that one in eight people currently alive will eventually die of cancer. Cancer manifests itself in a wide variety of forms, characterized by different degrees of invasiveness and aggressiveness. Malignant tumors are the second leading cause of death in the United States, after heart disease. 87% of cancer diagnoses in the U.S. are in people age 50 and older. But aging is not an intrinsic, irrevocable component of life. It can be manipulated just like other biological processes. Aging is a pathophysiological phenomenon that is possible to influence so as to delay or postpone the aging process, and in turn, delay the onset and incidence of various cancers. A recent and better understanding of the mechanisms of aging and longevity and the finding of particular pharmological agents that can extend lifespans and healthspans in other organisms, reveals that the aging process is malleable. The prospect of achieving a longer life, free of age related functional decline and fragility, such as cancer, is perhaps the quinessential long-felt but unsolved problem of mankind.

Aging is currently stimulating intense interest of both researchers and the general public. In developed countries, the average life expectancy has increased by roughly 30 years within the last century, and human senescence has been delayed by around a decade. The proportion of people over 60 is rising faster than any other age group in developed nations around the world. Seniors are expected to be one-fifth of the global population by 2050, double the proportion in 2017. Thus, one general objective of various embodiments of the present invention is to provide scientifically sound ways to help our aging population live healthier for longer. Although aging is arguably the most familiar aspect of human biology, its proximate and ultimate causes have not been fully elucidated. Consumption of tomato fruits, like those of many other plant species that are part of the human diet, is considered to be associated with several positive effects on health. Indeed, tomato fruits are an important source of bioactive compounds with known beneficial effects including vitamins, antioxidants, and anticancer substances. In particular, antioxidant metabolites are a group of vitamins, carotenoids, phenolic compounds, and phenolic acid that can provide effective protection by neutralizing free radicals, which are unstable molecules linked to the development of a number of degenerative diseases and conditions.

Aging is accompanied by a chronic, low grade, inflammatory status, resulting from an imbalance between pro- and anti-inflammatory processes, a pathogenic condition that is critical in the onset of certain major age-related chronic diseases, including atherosclerosis, type 2 diabetes, and neuro-degeneration. One goal of healthy aging and longevity relates to how best to achieve a lower propensity to accumulate inflammatory responses. Increasingly, there is a growing awareness of the importance of the variation in the gut microbiota as its affects the etiology of several age-related diseases, including cancer. Skeletal muscle atrophy is a nearly universal consequence of cancer. Cachexia is a positive risk factor for death, meaning if the patient has cachexia, the chance of death from the underlying condition is increased dramatically. Cachexia is considered the immediate cause of death of a large proportion of cancer patients, ranging from 22% to 40% of the patients. The pathogenesis of cancer cachexia is poorly understood. It is believed that multiple biologic pathways are involved, including proinflammatory cytokines and tumor-specific factors such as proteolysis-inducing factor. Muscle atrophy is believed to occur by a change in the normal balance between protein synthesis and protein degradation. During atrophy, there is a down-regulation of protein synthesis pathways and an activation of protein breakdown pathways. Only limited treatment options exist for patients with clinical cancer cachexia. Current treatment strategies involve attempting to improve an individual's appetite using appetite stimulants and protein supplementation to provide the individual with required nutrients. The reversal of cancer cachexia and muscle wasting leads to prolonged survival, and with the ability to retain muscle mass and strength, it is believed that various forms of cancer treatment may be more effective, if only due to the fact that the cancer victim may be able to withstand the rigors of the various cancer treatments involved. There is presently, however, an absence of effective medical therapies to prevent or reverse skeletal muscle atrophy, and especially therapies that involve reliance on a modification of a patient's microbiome. Current treatment recommendations to address skeletal muscle atrophy (e.g. physical rehabilitation, nutritional optimization, and treatment of underlying disease) are often ineffective and/or unfeasible and at present, a pharmacologic therapy does not exist. Thus, a treatment for skeletal muscle atrophy associated with cancer represents a very large unmet medical need and addressing the same is believed to not only extend an individual's lifespan, but also their healthspan.

What has been long desired throughout human history is a way to treat, inhibit or reduce the aging of a human, thereby also reducing the incidence of age related diseases and symptoms, such as cancer. The present invention in its various embodiments as described herein provides a method and system to extend the healthspan and lifespan of humans, providing a method and system to delay the onset of various cancers and to otherwise treat or prevent cancer.

SUMMARY OF THE INVENTION

Extending healthy life by slowing aging is the most efficient way to combat fatal and disabling pathologies, such as cancer, that plague the elderly human population. Thus, one aspect of the present invention is directed not to overcoming age-associated pathologies one-by-one, but rather, to prevent or delay age-related pathologies in general, thus more effectively addressing the commonplace chronic disorders experienced by the elderly. The present invention therefore represents a paradigm shift in the current public health strategy, which is targeted to the prevention of particular disorders, which even if successful, leaves an individual susceptible to other comorbidities that inevitably substitute for the pathology being treated. In various embodiments of the present invention, a method and system is provided that treats age-related disease by increasing the healthspan of a human individual. In various embodiments, rapamycin (sirolimus) is administered to an individual via a person's microbiome by employing microbes, and in particular bacteria modified to produce rapamycin and preferably other anti-aging agents, to achieve this objective.

As described in more detail herein, one aspect of the present invention involves the use of a natural small molecule derived from tomato plants, tomatidine, which is believed to cause cell growth, especially in skeletal muscle tissue. Tomatidine is an inhibitor of muscle atrophy and thus has a use as a therapeutic agent for skeletal muscle atrophy. Tomatidine is a steroidal alkaloid and the aglycone of alpha-tomatine, an abundant glycoalkaloid in tomato plants that mediates plant defense against fungi, bacteria, viruses and predatory insects. When consumed by animals, alpha-tomatine is hydrolyzed by stomach acid and intestinal bacteria to tomatidine, which is absorbed by the gut. Tomatidine is believed to have an anti-atrophic (anabolic) effect in skeletal muscle and possesses anti-hyperlipidemic and anti-atherosclerotic effects without evidence of toxicity. Tomatidine is significantly more potent than ursolic acid in building muscle tissue and has a different mechanism of action.

The tomato belongs to the Solanaceae family that includes more than 3,000 species. Tomato fruit consumption has been associated with a reduced risk of inflammatory processes, cancer, and chronic noncommunicable diseases (CNCD) including cardiovascular diseases (CVD) such as coronary heart disease, hypertension, diabetes, and obesity. Tomatidine is found in certain plants at certain developmental stages, such as in green (but not ripened red) tomatoes. One aspect of the present invention is directed to the provision to individuals in need thereof with bacteria that have been modified to produce effective amounts of tomatidine to address the muscle atrophy associated with various cancers. In one embodiment, DNA encoding tomatidine or its analogs is inserted into the genome of one or more bacterial species by employing CRISPR-Cas or Cfl1 systems, such that an individual can orally take a pill containing such modified bacteria (preferably bacteria of the same species as presently reside in the individual's gut microbiome) and in such a manner, administer tomatidine to the individual in a manner that does not require injections or the taking of traditional pharmaceutical formulations containing tomatidine. In such a manner, the production by such bacteria inside the individual provides a more natural way for tomatidine to be provided to those in need of its extraordinary abilities to foster the retention of muscle mass in the individual. The ability to further modify the populations of bacteria inside an individual via the use of particular antibiotics, for example, those that can target the modified species that produce tomatidine, provides a way to control the amount of tomatidine in the individual's body. Tomatidine in this instance, is but one of many examples of how the personal microbiome of an individual can be amended, modified, enhanced and/or changed to adjust the levels and amounts of various compounds, drugs, molecules, etc. that are important in maintaining or restoring health to an individual.

Treatments for various types of cancer are desired that relate to the production of competently folded p53 tumor support factor. There has been a long felt but unmet need for a way to inexpensively administer desired amounts of p53 protein to an individual in need thereof. The present invention in several of its aspects addresses this concern, for example, by the expression of p53 by human microbiome bacteria. In certain embodiments of the present invention, a method for treating cancer cachexia involves the administering to the microbiome of a subject in need thereof an effective amount of a bacterial combination that expresses p53 protein and tomatidine, such cancer being for example, one of breast cancer, bladder cancer, kidney cancer, or colorectal cancer. In certain embodiments, the cancer is a metastatic cancer; and the microbiome is one or more of the gut microbiome, the oral microbiome or the skin microbiome. Other embodiments involve mucosally administering to the subject an effective amount of a bacteria that has been modified to express one of tomatidine and p53, with the bacteria selected from the group consisting of—*Streptococcus, Actinomyces, Veillonella, Fusobacterium, Porphromonas, Prevotella, Treponema, Neisseria, Haemophilus; Eubacteria, Lactobacterium, Capnocytophaga, Eikenella, Leptotrichia, Peptostreptococcus, Staphylococcus, Streptococcus thermophilus* and *Propionibacterium*. Still other embodiments include the provision of *Streptomyces hygroscopicus* in an amount effective to produce therapeutically effective amounts of rapamycin to the subject. It should be appreciated that a therapeutically effective amount is preferably an amount sufficient to elicit any of the listed effects of natural tomatidine and p53, for example, including, but not limited to, the power to treat cancer cachexia in a fashion demonstrated by result indicating the maintenance of muscle mass in the individual treated. In preferred embodiments, the mucosal administration is oral administration and the subject individual maintains or increases muscle mass. In most preferred embodiments, the bacterial composition has been modified via a CRISPR-Cas or Cfl1 system to express tomatidine, and in other embodiments, produces both tomatidine and p53 protein. Other embodiments include a bacterial composition that includes one of a *Chlamydia* species, or *Shigella flexneri, Mycoplasma* bacteria, and *H. pylori*.

With respect to combating aging, particular agents and combinations thereof are employed in various embodiments of the present invention such that the incidence of cancer is lessened due to the avoidance of aging. Certain embodiments involve the administration of microbes to an individual where such microbes have been modified to produce desired levels of such agents/combinations. Since signaling pathways related to the aging of *Caenorhabditis elegans* (*C. elegans*), fruit flies and mice are evolutionarily conserved, compounds and agents extending lifespan in such organisms are believed to be useful in treating age-related diseases in humans. Natural products are preferred as they have a special resource advantage with few side effects. For example, microbes can be introduced to an individual's microbiome so that that they may produce one or more of such desired natural product agents by an individual's microbiome. One such agent is rapamycin (aka sirolimus), which is a macrolide produced by the bacterium *Streptomyces hygroscopicus*. Sirolimus is currently used as an immunosuppressant and is most often used to prevent rejection of transplanted organs. Sirolimus has two approved indications—renal transplantation and lymphangioleiomyomatosis and has also been shown to be potentially effective in treating Tuberous Sclerosis Complex (TSC)-associated seizures, skin disease, brain lesions, pulmonary lesions, and renal lesions. Administration of therapeutically effective amounts of rapamycin via an individual's microbiome (whether oral vaginal, skin, gut, bladder, etc.) forms one aspect of various embodiments of the present invention. Such employment of an anti-aging medicine like rapamycin is believed to be one of the most effective ways to combat various age-associated diseases of aging people. Rapamycin is but one example of the many compounds with anti-aging activity that have been and will be discovered. Delivery of such agents by employing an individual's microbiome is believed to be an efficient and person-specific way to account for the vast diversity of individual's biological systems, including the acknowledged disparity and array of microbiome compostions.

Rapamycin is an inhibitor of mTOR complex (mammalian target of rapamycin) which is a serine threonine kinase and a master regulator of protein synthesis, cell growth, and cell metabolism. Excessive mTORC1 activity has been implicated in multiple disease conditions, as well as various cancers, inflammatory bowel disease, inflammatory skin diseases and neurodegenerative diseases. In various embodiments, rapamycin is employed, especially when produced by microbes in an individual's microbiome, to treat or prevent disease conditions by inhibiting the mTORC1 pathway.

In certain embodiments, and while not bound by theory, it is believed that tomatidine increases the ability of an individual to maintain muscle mass, while rapamycin, as an inhibitor of mTOR, which increases the production of muscle proteins, reduces the growth of muscles. It is believed that these two agents may play parallel but separate roles in muscle atrophy, and thus, the use of both of these agents to address cancer, cachexia and aging is one particular aspect of the present invention.

In the treatment of particular cancers, the employment of rapamycin to inhibit cell growth, especially muscle growth, may in various instances be desired. At the same time, retention of muscle mass may be important for an individual to withstand the rigors of various cancer treatments. By administering tomatidine to an individual to maintain desired muscle mass, while also co-administering rapamycin to such individual to inhibit the growth of certain cells, especially cancer cells, one is able to achieve the seemingly converse objectives of maintaining muscle mass so as to preserve the health of an individual, while simultaneously defeating the undesired growth of cancer cells by the administration of effective amount of rapamycin to inhibit such undesired growth.

As described herein, p53 has apotptic characteristics and effectively keeps cancer growth in check by preventing cells from growing uncontrollably. In a somewhat similar manner, rapamycin also may be employed to regulate growth (e.g. by inhibiting growth of particular cells). Thus, the combination of rapamycin and p53 expression via cells of an individual;s microbiome provides two agents that are critical components in cell growth and apotosis events at the core of cancer treatments. Effective administration of cells (or microbes) of a person's microbiome via the purposeful administration of such cells (which have been modified, preferrably via CRISPR-Cas systems) to express therapeutically effective amounts of either or both p53 and rapamycin, is believed to provide an effective treatment for various cancerous conditions.

It is noted that caloric restriction would seem to negatively affect the growth of an organism and detrimentally affect the protein expression that would otherwise ensue in a well-fed individual. Rapamycin is a growth inhibitor, and thus, one would similarly conclude that the employment of such an agent would reduce the expression of proteins, such as those that are employed to build muscle. Moreover, p53 is an agent that generates cell death via apoptosis, and thus, would be viewed as an anti-growth factor in terms of cell survival. And yet all three of these agents are considered instrumental in both the aging process as well as in cancer. As cancer and aging are linked on certain levels, so too are the above referenced agents. The employment of these agents, especially by their purposeful expression via an individual's modified microbiome, provides a unique and effective way in which to combat both cancer and aging.

Various embodiments of the present invention are directed to a method for treating, inhibiting, or reducing aging, an age-related symptom, and/or an age-related disease (e.g. cancer) in a subject which comprises administering to the subject a therapeutically effective amount of a compound that has anti-aging characteristics, with administration being preferably via an individual's own microbiome. Included, but not limited to such a list of compounds is rapamycin, p53 and tomatidine.

The administration of such compounds/agents via an individual's microbiome is believed to positively affect the extending of the lifespan of an individual, and especially effective in delaying the onset of age-related diseases and conditions, such as cancer, thus extending the healthspan of the individual from what it otherwise would have been if such administration was not performed. The particular effective amount of such agents/compounds, such as rapamycin (including analog or derivatives thereof) depend upon the disease to be treated, the length of duration desired and the particular characteristics of the individual's microbiome—and which of the one or more various microbiomes of the person may be the source of the administration. In certain embodiments where the agent/compound comprises rapamycin or an analog thereof, administration of rapamycin may be performed to effect about 0.001 mg to 30 mg total per day as an effective dose, preferably at least about 0.1 mg per day, with a preferred blood level of rapamycin in the subject being about 0.5 ng per mL whole blood after administration of the composition after a 24 hour period. By administering antibiotics that target the particular microbes that produce such agents/compounds (e.g. rapamycin) one can address overproduction by such microbes by killing the microbes producing such agents. Various other embodiments are directed to the skin microbiome of a person so as to address diseases of the skin, including but not limited to skin cancer. The lactic acid bacteria *Streptococcus thermophilus* has been found to increase ceramide production in the skin. Ceramides are known to play an essential role in structuring and maintaining the water permeability barrier function of skin. With aging, the total ceramide content of skin, along with the skin's ability to function as a barrier, decreases. Certain embodiments are directed to ceramide supplementation via a subject's microbiome to improve skin barrier function.

Certain embodiments are directed to a method of treating bladder cancer in a subject in need of such treatment, such method comprising administering to a microbiome of a subject with bladder cancer an effective amount of a bacterial composition comprising *bacillus calmette-guerin*, with the bacterial composition adapted to produce tomatidine and rapamycin. Preferably, the bacterial composition comprises bacteria modified via a clustered regularly interspaced short palindromic repeats (CRISPR) CRISPR associated protein (Cas) system to express one or both of tomatidine and rapamycin. Certain embodiments are focused on treating metastatic bladder cancer. The microbiome employed may be the gut, oral, bladder or skin microbiome. Certain embodiments further include employing a microbe selected from the group consisting of *Streptococcus, Actinomyces, Veillonella, Fusobacterium, Porphromonas, Prevotella, Treponema, Nisseria, Haemophilis, Eubacteria, Lactobacterium, Capnocytophaga, Eikenella, Leptotrichia, Peptostreptococcus, Staphylococcus*, and *Propionibacterium*. One preferred embodiment involves administering a bacterial composition to the subject so that at least 0.1 mg of rapamycin is provided to the subject each day. Preferably, the bacterial composition is modified via a CRISPR-Cas system to express one of rapamycin and/or tomatidine, with preferred bacterial compositions including one of a *Chlamydia, Shigella flexneri, Mycoplasma* bacteria, and *H. pylori*. In other preferred embodiments, the method comprises administering to a microbiome of a subject with bladder cancer an effective amount of a bacterial composition comprising a bacteria that has been modified to express a therapeutically effective amount of tomatidine and rapamycin, with the bacteria selected from the group consisting of *Streptococcus, Actinomyces, Veillonella, Fusobacterium, Porphromonas, Prevotella, Treponema, Nisseria, Haemophilis, Eubacteria, Lactobacterium, Capnocytophaga, Eikenella, Leptotrichia, Peptostreptococcus, Staphylococcus, Propionibacterium, Chlamydia, Shigella flexneri, Mycoplasma* bacteria, *H. pylori*, and *Streptomyces hygroscopicus*. The bacteria employed may be of a species found in the subject's gut microbiome and may further have been modified using a CRISPR-Cas system to produce one of tomatidine or rapamycin. A therapeutically effective amount of a bacterial composition may also include *Streptomyces hygroscopicus* in an amount effective to provide a therapeutically effective amount of rapamycin to the subject. In particular embodiments, especially directed to addressing bladder cancer, the bacterial composition comprises *bacillus calmette-guerin*, and even more preferably, where the *bacillus calmette-guerin* also produces at least one of p53, rapamycin or tomatidine, and especially where the method maintains or increases the muscle mass of the subject. As described in more detail in the detailed description of various embodiments, still other agents, such as methylene blue, metformin, resveratrol (3,4',5-trihydroxystilbene; $C_{14}H_{12}O_3$), p53 protein, spermidine, diallyl trisulfide, apigenin, cyclopamine, sulforaphane, curcumin and glucosamine are employed via the production by microbes of an individual's microbiome to achieve the objective of delaying aging, and thus, in delaying and treating the onset of cancers.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, pictures, etc. will provide a basis for the scope of the present invention as it may be claimed now and in future applications. While embodiments of the invention have been illustrated and described, it is not intended that these embodiments illustrate and describe all possible forms of the invention. Rather, the words used in this specification are words of description rather than limitation, and it is understood that various changes may be made without departing from the spirit and scope of the invention.

DETAILED DESCRIPTION OF CERTAIN EMBODIMENTS OF THE INVENTION

Figure 1:
FIG. 1 is a picture of Ponce De Lion, the famed Spanish explorer who allegedly sought the Fountain of Youth.
Figure 2:
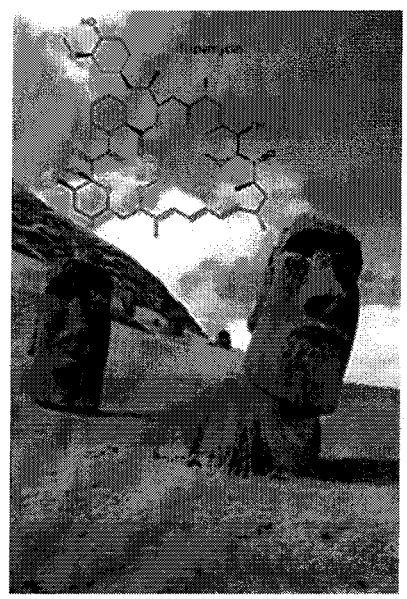
FIG. 2 is a depiction of the chemical structure of rapamycin set against the backdrop of monuments on Easter Island, from which rapamycin was discovered.

The forgotten organ—the human microbiome—comprises a community of microorganisms that colonizes various sites of the human body. Through coevolution of bacteria, archaea and fungi with the human host over thousands of years, a complex host-microbiome relationship emerged in which many functions, including metabolism and immune responses, became codependent. This coupling becomes evident when disruption in the microbiome composition, termed dysbiosis, is mirrored by the development of pathologies in the host. Among the most serious consequences of dysbiosis, is the development of cancer. Various embodiments of the present invention are directed to the field of Oncology, and in particular, embodiments directed to a method of ameliorating, treating, or preventing a malignancy in a human subject wherein the steps of the method assist or boost the immune system in eradicating cancerous cells. In certain embodiments, administration of beneficial bacteria to an individual's microbiome that have been modified so as to produce effective amounts of desired compositions, compounds, agents, e.g. tomatidine, p53 protein, etc., is employed to address cancerous conditions. In several embodiments, the administration of such beneficial bacteria and microbes to an individual's microbiome invokes either an active (or a passive) immune response to destroy, weaken or render less invasive certain cancerous cells, and preferably maintains muscle tissue to combat cancer cachexia.

Various embodiments of the present invention involve the expression/production by microbes of an individual's microbiome of a phytochemical to enhance the lifespan and health of a human. Phytochemicals are chemicals produced by plants, and include tannins, lignins, and flavonoids. The largest and best studied polyphenols are the flavonoids, with more than 8,000 identified and classified into at least six subgroups: flavonols, flavones, flavanones, flavanols (and their oligomers, proanthocyanidins), anthocyanidins, and isoflavonoids. About 100 polyphenols are in foods humans typically eat. Flavonoids are widely distributed in plants and function as plant pigments, signaling molecules, and defenders against infection and injury. Further support for the theory underlying the mechanism of action of certain embodiments of the present invention can be discerned from an appreciation that various fruits and vegetables produce phytochemicals that have been touted as having various beneficial effects, often believed to be noxious agents that dissuade insects and other organisms from consuming the plants. Phytochemicals that activate adaptive cellular stress response pathways typically have a bitter taste and some are known to activate the Nrf2 antioxidant response pathway, such as curcumin. Often plants concentrate phytochemicals in particular parts of the plant that are exposed to the environment, such as the skin of the fruit/vegetable, or that are involved in the production of seeds. Tomatidine is present in high amounts in the unripe tomato, with its amount plummeting when the tomato ripens, which is consistent with the role of tomatidine protecting the unripe fruit from consumption, followed by a drop of tomatidine presence in the skin with ripening, enabling the consumption of the ripe fruit and the subsequent dispersal of seeds by animals and insects that eat the fruit. It is believed that tomatidine activates adaptive cellular stress responses in muscle cells that protect such cells against metabolic and oxidative stress, thus counteracting age-related dysfunction and degeneration. Other vegetables may possess similar steroidal alkaloids similar to tomatidine that serve the same purpose. For example, it is believed that potatoes and eggplant express Solanaceae family compounds that serve such purposes. By inducing mitophagy, tomatidine preserves cellular function during aging and leads to an individual being more free from age related diseases. Similarly, quercetin is a flavonol compound that is found in many fruits and vegetables, such as red onions, capers, black plums, blueberries, and red applies. It has been reported to provide numerous health benefits to humans that ingest the compound. These reported health benefits include acting as a powerful antioxidant, improving athletic performance, improving cardiovascular health, and aiding in immune response. Quercetin can reduce blood pressure and LDL cholesterol and increase athletic performance.

One aspect of the present invention is directed to employing tomatidine to enhance the lifespan and health of a human (or a mammalian pet) by administering tomatidine in a fashion, e.g. via the individual's microbiome, to inhibit age related skeletal muscle atrophy. While not bound by theory, it is believed that such administration of tomatidine extends the lifespan and healthspan of humans and other mammals by inducing mitochondrial hormesis via the induction of ROS production. This further entails the activation of certain cellular and antioxidant pathways, including the SKN-1/Nrf2 pathway, which results in increased mitophagy. The selective removal of damaged or dysfunctional mitochondria by mitochondrial autophagy, termed mitophagy, is believed to be a feature of a treatment to extend an individual's lifespan in a safe and effective manner. Mitophagy modulates bioenergetics and survival in various diseases by reducing redox and damage. Impaired mitophagy occurs in physiological aging, as well as in certain diseases, such as sarcopenia and also believed to be present in cachexia.

In certain embodiments, the administration or delivery of certain noxious chemicals are believed to counteract aging and age related disease by inducing adaptive hormetic stress responses in cells. In other embodiments, the inclusion of rapamycin administration is employed to improve the healthspan of humans as it is further related to mitophagy. The methods and systems as set forth herein are directed to the extension of human life span in a fashion that promotes healthy aging and counteracts disease processes related to age-related diseases.

Tomatidine administration as described in the present specification is believed to contribute to a delay in the physiological aspects of aging. For example, it is believed that tomatidine increases mitochondria DNA content and muscle fitness and lowers adiposity, as well as decreases skeletal muscle atrophy. While not bound by theory, it is believed that the administration of tomatidine maintains homeostasis by modulating mitochondrial biogenesis and induces mild oxidative stress, which activates the above referenced pathways to induce mitophagy. The amount of tomatidine administered is believed to be important to achieve its desired age fighting effects, with at least about 10 micro-mole, and more beneficially with between about 25 micro-mole and 50 micro-mole being preferred. Moreover, administration of tomatidine is believed to increase the production in an individual of amounts of certain amino acids, such as free amino acids of leucine, threonine, tryptophan, arginine, histidine, valine, isoleucine, and methionine. Such administration is also believed to affect ROS regulation and metabolism. As aging is known to negatively affect mitochondrial quality and biogenesis, the use of tomatidine to enhance mitophagy can be employed to reduce the amount of neurodegeneration and cellular dysfunction of cell metabolism, especially by inducing an increase in Nrf2/ARE reporter activity. Upon activation by ROS, Nrf2 translocates from the cytoplasm of a cell to the nucleus, where it binds to the ARE region to transcriptionally activate genes encoding antioxidant proteins. Thus, tomatidine administration activates the Nrf2-ARE pathway by inducing cells to increase levels of ROS, resulting in the contribution to mitophagy induction. While not bound by theory, it is also believed that administration of tomatidine as described herein acts via multiple stress response pathways, such as, in addition to the Nrf2 pathway referenced above, through the activation of the mitochondrial unfolded protein response (UPR-mt). Compromised mitochondrial quality and function is related to pathological aging and disease and the accumulation of damaged mitochondria within cells triggers apoptosis, inflammation and cell senescence. Sarcopenia is observed in aging individuals, with almost 25% of those over 60 years old experiencing the same, rising to over 50% by the age of 80.

Tomatidine is believed to preserve muscle function during aging and therefore extends lifespan by improving mitochondrial quality by reducing muscle atrophy. Sarcopenia is therefore common in aging and is associated with the deterioration of muscle fiber cells and with infiltration of adipocytes and inflammatory immune cells, impairing the generation of new myocytes. In various embodiments of the present invention, the employment of tomatidine is not resultant from effects on muscle stem cells or immune cells, but rather, is directed to the effect that tomatidine has in influencing the muscle cells themselves as it is believed that the mechanism of action is directed to processes occurring within skeletal muscle fiber cells.

Various aspects of the present invention are directed to the induction of mitophagy by the administration of tomatidine, especially via the microbiome cells of an individual as otherwise described herein, so as to enhance the quality of the cellular mitochondrial pool and/or mitochondrial biogenesis. Support for this theory of action can be found, for example, in studies of premature aging disease, such as Hutchinson-Gilford progeria syndrome, caused by a mutation of the nuclear architectural proteins lamin A and C. Such patients showed profound growth delay and premature aging phenotypes, including cardiac muscle and skeletal muscle pathologies. It is known that Nrf2 activity contributes to premature aging and that activation of the Nrf2 pathway ameliorates such disease. One aspect of the present invention is therefore directed to the administration of tomatidine, in particular as described herein via expression by various bacteria in an individual's microbiome, so that it triggers mitophagy and induces Nrf2 activation. A signaling role for ROS in the stimulation of mitophagy in cells under mild stress supports the use of tomatidine as described herein, as moderately elevated ROS levels have been seen as inducing mitophagy, which has the effect of clearing aged or dysfunctional mitochondria. If ROS levels are too high, however, or if mitophagy is compromised, mitochondrial dysfunction becomes exacerbated, demonstrating that ROS levels have a dynamic role in health and aging disease. Employment of tomatidine to achieve a moderate elevation of ROS levels is therefore one objective of various embodiments of the present invention, but with care not to achieve excessive ROS levels, thus accomplishing the desired goal of enhancing cellular stress resistance in a manner that is disease protective. Tomatidine is therefore preferably administered in effective amounts that induce a moderate increase in ROS levels that is necessary to trigger mitophagy without demonstrating mitochondrial dysfunction.

Tomatidine is not believed to have significant anti-microbial effects, at least when used alone. When co-administered with other compounds, however, it is believed that there is a synergistic effect and therefore, tomatidine is viewed as an antibiotic potentiator when used with ampicillin, etc. Preferably, tomatidine, in certain embodiments is used at a concentration of about 200 micro grams per mL. Thus, in several embodiments, the use of tomatidine administration in an individual is employed to synergistically enhance the action of various antibiotics against certain bacteria. Such synergistic effects are believed to be also accomplished when tomatidine expression/administration in an individual is coupled of the co-administration with at least one of the following: p53 protein, rapamycin, resveratrol, metformin, spermidine, glucosamine and methylene blue.

In one embodiment, a person is provided with beneficial microbes that are adapted to produce therapeutic amounts of tomatidine to achieve the stimulation of skeletal muscle anabolism, leading to muscle hypertrophy, increased strength and improved exercise capacity. Preferably, tomatidine is produced by such microbes, preferably by a person's gut bacteria, in a manner effective to increase skeletal muscle and to decrease fat of such individual, due to tomatidine's ability to limit the progression of skeletal muscle atrophy.

One aspect of the present invention is directed to the provision to a person, via their oral and/or gut or other microbiomes, of effective amounts of tomatidine that is produced from the microbes in that individual's microbiome such that the microbes promote the growth of larger muscles, but without increasing overall body weight. It will be appreciated that still other aspects of the present invention involve the treatment of obesity (as well as cancer) by providing certain amounts of tomatidine via a person's microbiome to facilitate muscle mass increases while at the same time, decreasing the amount of fat weight of the individual being administered the tomatidine. While treatment of obesity is one possible application of the present invention, a principal objective is to describe embodiments directed to the abatement of muscle mass loss by those suffering from cancer.

Other aspects of the present invention relate to the reduction of the likelihood of, treatment and/or prevention of cancer by interrupting a microbial carcinogenic pathway, and by enhancing an individual's survival by addressing the muscle atrophy associated with cancer. Various embodiments of the present invention use microbiota modifications to improve the efficacy of existing treatments, and in particular, the provision of tomatidine via the production by a patient's microbiome is one aspect of how to address the treatment and prolonged survival of cancer victims.

Preferably, the modified bacteria employed in the present invention are administered orally to a patient in order to deliver the therapeutic directly to the site of inflammation in the gut. The advantage of this approach is that it avoids systemic administration of immunosuppressive drugs and delivers the therapeutic directly to the gastrointestinal tract. The viability and stability of such modified bacteria is enhanced to support the production of such microbes of desired agents/compounds, e.g. tomatidine, p53 protein, rapamycin, resveratrol, methylene blue, etc. and by doing so, a method is provided that reduces gut inflammation, enhances gut barrier function, and/or treats autoimmune disorders. Preferably, such modified bacteria are capable of producing therapeutic anti-inflammation and/or gut barrier enhancer molecules, particularly in the presence of reactive nitrogen species, and more preferably the bacteria are functionally silent until they reach an environment containing local RNS, wherein expression of the therapeutic molecule is induced. In certain embodiments, the genetically engineered bacteria are non-pathogenic and may be introduced into the gut in order to reduce gut inflammation and/or enhance gut barrier function. For example, in some embodiments, the bacteria are under the control of a RNS-responsive regulatory region and a corresponding RNS-sensing transcription factor such that a desired product, e.g. butyrate is produced, which induces the differentiation of regulatory T cells in the gut and/or promotes the barrier function of colonic epithelial cells. Short-chain fatty acid production by commensal bacteria is important in regulating the immune system in the gut. Butyrate plays a direct role in inducing the differentiation of regulatory T cells and suppressing immune responses associated with inflammation. Butyrate is normally produced by microbial fermentation of dietary fiber and plays a central role in maintaining colonic epithelial cell homeostasis and barrier function. Use of such modified bacteria, especially those modified via CRISPR-Cas systems, provides a way to generate a desired therapeutic effect in a manner that lowers the safety issues associated with systemic exposure.

Resveratrol (3,4',5-trihydroxystilbene; $C_{14}H_{12}O_3$) is a polyphenolic phytoalexin found in grapes, berries, peanuts, and wines. Resveratrol has been viewed as an antioxidant, anti-inflammatory, anti-apoptotic, and anticancer agent. Moreover, it has been reported that resveratrol modulates mitochondrial function, redox biology, and dynamics in both in vitro and in vivo experimental models. Resveratrol also attenuates mitochondrial impairment induced by certain stressors. Resveratrol upregulates, for example, mitochondria-located antioxidant enzymes, decreasing the production of reactive species by these organelles. Resveratrol also triggers mitochondrial biogenesis, ameliorating the mitochondria-related bioenergetics status in mammalian cells. Brain cells (both neuronal and glial) are susceptible to mitochondrial dysfunction due to their high demand for adenosine triphosphate (ATP). Additionally, brain cells consume oxygen ($O_2$) at very high rates, leading to a proportionally high mitochondrial production of reactive species. One aspect of various embodiments of the present invention is the maintenance of mitochondrial function in various cell types to address degenerative diseases, which involve mitochondrial impairment and increased generation of reactive species, leading, for example, to neuroinflammation and cell death. The mechanism by which resveratrol protects mitochondrial function and dynamics is not completely understood, but it is known that resveratrol is able to induce cytotoxicity depending on its dosage. Resveratrol produced by the microbiome of an individual can be employed to improve the dysregulation of the gut microbiota induced by a high-fat diet, as it will result in increasing the ratio of Bacteroides-to-Firmicutes and also increases the growth of lactobacillus acidophjilus and bifidobacterium in humans. It is believed that resveratrol modifies the intracellular environment by changing the oxidizing milieu into a reducing milieu and upregulates intracellular glutathione, potentiating a signal transduction cascade that results in mitophagy, and thus paves the way to an anti-aging environment. Rapamycin was first discovered in Easter Island soil bacteria in the 1980s. It is known that rapamycin extends the life span of mice. The protein that rapamycin targets is a kinase called mTOR. This kinase plays a role in a variety of pathways. mTOR suppresses some senescent cells from secreting their cocktail of problematic molecules and mTOR plays a role in the positive effects of caloric restriction. But given the disparity of microbiome constituents between any two individuals, the present inventors contend that the manner by which to effectively address aging of any particular individual lies in taking advantage of the noted differences of each individual's microbiome to address the aging mechanisms involved.

Mammalian/mechanistic target of rapamycin (mTOR) is an intracellular protein complex that is responsive to both growth factors and nutrient availability, and which also impacts mitochondrial function. It is comprised of the TOR kinase—known as mTOR in mammals. The TOR signaling pathway is highly conserved in eukaryotes and is functionally defined as the target of the highly-specific antifungal, rapamycin. mTOR and aging appear to have co-evolved, suggesting that cancer is inexorably linked to fundamental aspects of life. Rapamycin can be employed, via production by an individual's microbiome, to achieve the objective of delaying the effects of aging and thus, reduce diseases associated with aging. Rapamycin can be used to address one of the deepest mysteries of life, aging. Age-associated diseases interface with TOR and its signaling systems, and thus, employment of rapamycin (alone or in concert with the various other agents described herein) provides the ability to target both aging and its associated diseases, including cancer.

In certain embodiments, rapamycin is administered via an individual's own microbiome as a way to deliver an anti-aging treatment that works on everyone despite the distinct and acknowledged differences between humans. The differences of each individual's microbiome works in favor of this approach as delivery of rapamycin via one's own microbiome is naturally customed tailored as focusing on modification of an individual's microbiome provides desired anti-aging agents while maintaining the distinct character of an individual's microbiome. Aging is therefore possible to treat in a personalized way by taking into account the individual's unique microbiome. The present invention provides a way to tailor preventive measures and treatments to different individuals. Mechanical loading plays a major role in the regulation of skeletal muscle mass, and the maintenance of muscle mass profoundly influences health and quality of life. Signaling by the mammalian/mechanistic target of rapamycin (mTOR) is a key component of the mechanotransduction pathway. Employment of an individual's microbiome to administer effective amounts of rapamycin to the individual is one way in which to modulate mTOR signaling.

Given the importance of mTOR signaling in the maintenance of muscle mass, the use of rapamycin in combination with tomatidine to activate mTOR signaling, by employing an individual's own microbiome, can address cachexia, and in particular cancer cachexia so as to maintain an individual's muscle mass.

A variety of stimuli, such as nutrients, growth factors, and mechanical loading, can regulate protein synthesis in skeletal muscle. The regulation of translation initiation by these stimuli is mediated by mTOR, which exists in at least two characteristically distinct complexes; a) the rapamycin-sensitive mTOR complex 1 (mTORC1), and b) the rapamycin-insensitive mTOR complex 2 (mTORC2). The control of translation initiation by mTOR is one of the key steps for the regulation of protein synthesis in skeletal muscle. Rapamycin, a highly specific inhibitor of mTOR signaling, can prevent protein synthesis induced by various forms of mechanical loading such as resistance exercise. Rapamycin can prevent chronic mechanical overload-induced increases in fiber size (i.e., hypertrophy). Rapamycin-sensitive mTOR signaling plays a central role in the regulation of protein synthesis and muscle mass during periods of increased mechanical loading. mTOR is the rapamycin-sensitive element that confers mechanically induced muscle growth. Rapamycin exhibits growth inhibitory effects. mTOR, within skeletal muscle cells, is the primary rapamycin-sensitive element that confers a mechanically-induced hypertrophic response. The targeting of mTOR signaling is therefore critical in various methods directed to the prevention of muscle atrophy. mTOR is a crucial component in the mechanotransduction pathway that promotes muscle growth. mTOR signaling induces skeletal muscle growth via a rapamycin-sensitive mechanism. Mechanical loading activates mTOR signaling and muscle growth through a unique mechanism but the identity of this mechanism remains unclear.

Increased expression of tomatidine and rapamycin via an individual's microbiome can therefore mitigate various types of muscle fiber atrophy and may be employed to reduce if not prevent muscle atrophy. Skeletal muscles consume a lot of energy (i.e., ATP) during every cyclic interaction between actin and myosin, and importantly, these active muscles comprise approximately 45% of total body mass. As mitochondria are the source of ATP in humans and in view of the importance of mitophagy as described herein, the link between rapamycin and tomatidine with mitochondria and the retention of muscle mass of an individual can be discerned. Skeletal muscles can also play a critical role in the regulation of whole-body energy metabolism. Skeletal muscle mass is inversely associated with several metabolic disorders such as obesity, diabetes, and metabolic syndromes. Thus, the maintenance of skeletal muscle mass is not only keeping human bodies physically functional, but also metabolically healthy. As skeletal muscle functions are directly associated with its mass, and thus, the maintenance of skeletal muscle mass will contribute significantly to health and quality of life. Skeletal muscle mass is reduced with aging and both sedentary and active adults will lose up to 30-40% of their muscle mass, which is directly related to and is associated with disability, loss of independence, an increased risk of morbidity and mortality. While it is known that skeletal muscle mass can be increased by mechanical loading/stimuli (e.g., mechanical overload, etc.) in many individuals, there are problems with achieving such stimuli, including the simple human propensity for the avoidance of exercise. The present invention, in various aspects, provides an alternative, as well as a co-treatment, for those individuals who can not or who do not engage in mechanical loading/stimuli to preserve their muscle mass as they age, thus preventing muscle atrophy.

One aspect of various embodiments of the present invention relates to slowing the intrinsic rate of aging of a human by administering a therapeutically effective amount of an anti-aging agent, for example, rapamycin, preferrably solely via administration through the microbiome of an individual. Cancer and aging are inexorably linked. Rapamycin is not the potent immunosuppressant some have incorrectly concluded. Age is the greatest risk factor for nearly every major cause of mortality in humans. Prior efforts to improve the health of humans have been directed to curing diseases that spring up during old age, such as cancer and heart disease, rather than decoding the underlying cellular and molecular processes that make the elderly vulnerable to these afflictions in the first place. While humans are living longer, they are not always healthy enough to enjoy the extra years and therefore survive for years or decades with reduced quality of life. It has been observed that caloric restriction in a variety of organisms—including mice, flies, worms, and yeast—achieves an extended life span and activates cellular protection pathways. In humans, however, caloric restriction often results in a weakening of the immune system. In any event, it is a largely impracticable way to realistically achieve the goals of a long and healthy life. The present invention provides a better way. A comparison of stools from aged vs. young humans reveals that older frail folks had lower levels of short-chain fatty acids, which the microbes in our guts normally make from dietary fiber. These short-chain fatty acids, including acetate, butyrate, and propionate, are an important energy source for the colon. Frail subjects also had gut microbiomes depleted in species of bacteria that could do this chemical conversion. It has also been observed that cancerous cells often become senescent and secrete chemical messages to nearby cells, all the while ceasing division. When enough senescent cells accumulate, their combined chemical cocktail results in a variety of age-related problems, including heart disease.

Mitochondria are critical in understanding aging, as demonstrated by some of the first genes found to extend worm lifetimes coding for dysfunctional proteins in mitochondria.

The shortening of telomeres is also associated with aging, but attempts to use telomerase to help rebuild shortened ends often results in cancer. For most of human evolutionary history, a human's life span was extremely short and therefore, few died of old age diseases, such as cancer or heart disease. Evolution optimized most human traits so we could survive long enough to produce offspring. In the late 1990s, researchers discovered that simple mutations in single genes could double, triple, and even more radically increase the life span of worms and single gene mutations were also found that could extend life span in fruit flies and mice and other organisms. Some therefore believe that because simple genetic interventions can extend lifetimes and healthspans, targeting such genes will result in addressing aging. But such a route entails undesired human genetic manipulation. The present invention avoids such a dramatic tactic and achieves the desired and long-sought anti-aging objective via manipulation of an individual's microbiome, rather than their human DNA.

On Apr. 2, 1513, Spanish explorer Juan Ponce de León (See FIG. 1) and his crew became the first recorded Europeans to set eyes on Florida. Legend holds that they made this discovery while searching for the Fountain of Youth, a magical water source supposedly capable of reversing the aging process and curing sickness. Spanish sources asserted that the Taino Indians of the Caribbean also spoke of a magic fountain and rejuvenating river that existed somewhere north of Cuba. These rumors conceivably reached the ears of Ponce de León, who is thought to have accompanied Christopher Columbus on his second voyage to the New World in 1493.

In various embodiments, the administration of therapeutically effective amounts of rapamycin via an individual's microbiome (whether oral vaginal, skin, gut, etc.) is performed to extend the healthspan and lifespan of an individual. "The wiser mind mourns less for what age takes away than what it leaves behind." William Wordsworth Delivery of rapamycin by employing an individual's microbiome is believed to be an efficient and person-specific way to account for the vast diversity found between individuals with respect to the composition of their microbiomes, such as the type and ratios of bacteria in any particular individual's microbiome. For example, other embodiments are directed to a method of treating NAFLD by administering, via the microbiome of an individual, a therapeutically effective amount of rapamycin. Certain embodiments employ a dose of rapamycin in the range of 1 mg/day to 5 mg/day, and in other embodiments, in the range from about 0.01 µg/day to about 50 µg/day.

Such ability to tailor the administration of certain agents, such as rapamycin, by addressing the administration of the same via bacteria that may be somewhat unique to the individual, is one unique aspect of the present invention. Resveratrol is believed to activate the SIRT1 mechanism.

Figure 3:
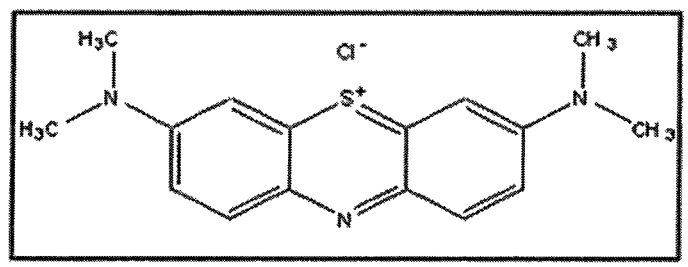
FIG. 3 is the chemical formula for methylene blue.
Figure 4:
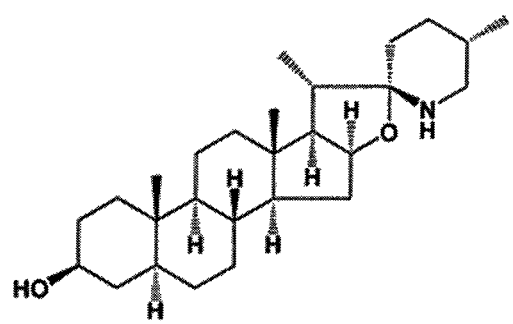
FIG. 4 is the chemical formula for tomatidine
Figure 5:
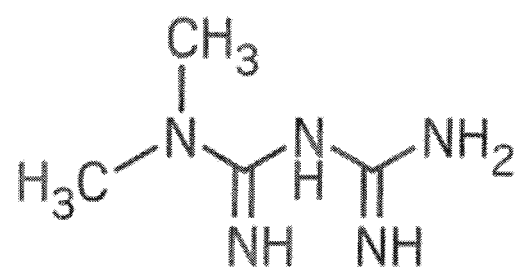
FIG. 5 is the chemical formula for metformin.

In various embodiments, an antioxidant called methylene blue (See FIG. 3), a common, inexpensive and safe chemical, is employed to slow the aging of human skin. Methylene blue is an inhibitor of nitric oxide synthase and guanylate cyclase and has many uses in medicine. Methylene blue is a common stain used by biologists to help them see bacteria and other forms of life under the microscope.

Methylene blue makes fundamental, long-term changes to skin cells and is a medicine as well as a dye. It was the first synthetic drug to be created and was originally used as a malaria treatment. It has previously been used to treat methemoglobinemia and neural problems, as well as to treat urinary tract infections. Production of methylene blue by an individual's microbiome in a fashion that promotes anti-aging is one aspect of the present invention.

Certain embodiments involve the administration of beneficial bacteria to an individual's microbiome that have been modified so as to produce effective amounts of desired compositions, compounds, agents, etc, e.g. tomatidine, p53 protein, rapamycin, resveratrol, methylene blue etc., to address an immune response. For example, in several embodiments, the administration of beneficial bacteria and microbes to an individual's microbiome invokes either an active (or a passive) immune response to destroy, weaken or render less invasive certain cancerous cells. Various other embodiments are drawn to the co-administration of one or more of tomatidine, p53 protein, rapamycin, resveratrol, methylene blue etc., in combination with conventional therapies for treating diseases, such as cancer. In particular, the co-administration of various pre-biotic compositions to enhance and sustain the desired effects of the beneficial modified bacteria forms another aspect of the present invention. In this regard, incorporation by reference of U.S. Patent publication No. 20160213702 to Maltzahn et al. is included as part of the written description of various aspects of the present invention. For example, in view of the fact that the microbiota of humans is complex and varies by individual depending on genetics, age, sex, stress, nutrition and diet, modifying the numbers and species of gut, oral, vaginal and skin microbiota can alter community function and interaction with the host. A number of probiotic bacteria known in the art, as well as some foods considered to be 'prebiotic' that contain substances that promote the growth of certain bacteria and that stimulate beneficial microbiota shifts to improve human health, can be employed in concert with the modified bacteria as described herein to effect desired cancer treatment regimens. For example, the administration of glycans in an amount effective to modulate the abundance of the bacterial taxa can be used to achieve better outcomes in the treatment of various age related diseases, including cancer.

It has been theorized for some time that mitochondria—the organelles that produce energy in human cells—play a role in aging and disease. There is evidence that people who experience less destructive aging have genetically different mitochondria when compared to the general population. Furthermore, mitochondrial lineages described by patterns of common genetic variants (or "haplogroups") have also been shown to be associated with increased longevity in different populations. The process of oxidative phosphorylation for ATP generation in mitochondria is the main source of reactive oxygen species (ROS) within the cell (about 90% of total ROS in cells). The limited repair capacity of mitochondrial DNA (mtDNA) makes them particularly vulnerable to accumulation of damages, with mutations in mtDNA resulting in increased ROS production, which causes diverse damages in the cells. The ROS vicious cycle is believed to account for an exponential increase in oxidative damage during aging. Senescent cells also increase with age and have been found at sites of age-related pathologies. Chronically active p53 both promotes cellular senescence and accelerates aging phenotypes.

Proper functioning of mitochondria, as the central organelle for metabolism and other cell signaling pathways, is required to maintain rapid growth and proliferation of cancer cells since tumor cells devoid of mitochondria grow very slowly. Increased amounts of lactate not only blocks acetyl-CoA metabolism in mitochondria, but also reduces mitochondrial biogenesis as well as oxygen consumption. Tumor suppressor, P53, plays an important role in promoting cell death as it is activated via a ROS-dependent pathway and leads to apoptosis in cancer. Inhibited cell growth and increased apoptosis in cancer by P53 activation are also regulated by miRNA or SIRT2 dependent pathways. Lactate-producing ('lactagenic') cancer cells are characterized by increased aerobic glycolysis and excessive lactate formation, a phenomenon described by Otto Warburg 93 years ago, which still remains unexplained. In 1923, Otto Warburg observed that cancer cells were characterized by accelerated glycolysis and excessive lactate formation even under fully oxygenated conditions. His discovery was subsequently named the 'Warburg Effect'. While the Warburg Effect is a hallmark of cancer, the study of cancer cell metabolism was diverted when investigators began to employ genomic techniques to better understand cancer biology. The cure for cancer through gene-based research, however, has yet to come to fruition, and the role of the Warburg Effect in cancer growth and carcinogenesis is still a mystery. One aspect of the present invention relates to the production of various agents by an individual's microbiome, including the use of lactobacterium that produce lactate. There has been a recent renewal of interest in lactate as a player in cancer as lactate is an obligatory product of glycolysis, an important metabolic fuel energy source, and an important signaling molecule. In lactagenic cancers, there is observed a decrease in mitochondrial function. Lactate production constantly occurs in skeletal muscles as lactate is the obligatory product of glycolysis. The rate of lactate production is greatly enhanced in working skeletal muscle and thus, it has been observed that during high-intensity exercise, working muscles display some of the same metabolic characteristics as do cancer cells. Certain aspects of the present invention are therefore directed to the employment of lactobacterium via introduction into an individual's microbiome, such that the levels of lactate can be achieved to address cancer conditions. Lactate metabolism in cancer can therefore be addressed via manipulation of a subject's microbiome to treat cancer conditions. Cancer cells move away from an efficient metabolic mechanism and employ an inefficient pathway producing two cytosolic ATPs per molecule of glucose instead of ~36-38 ATPs via coupled mitochondrial respiration. Mitochondrial dysfunction is disastrous for lactate clearance in cancer. Damaged mitochondria are responsible for increased production of reactive oxygen species, metabolic inflexibility, and inflammation.

A number of compounds have been found to stimulate autophagy, including rapamycin, resveratrol, metformin, spermidine, and glucosamine. mTOR, the mammalian target of rapamycin, is considered to be a major checkpoint in a pathway linking the cellular nutritional state with the level of ongoing autophagy. Mitochondria can be selectively targeted for degradation via macroautophagy (mitophagy). Induction of autophagy is an important homeostatic mechanism that is disrupted in dystrophic muscles. Autophagy is a cellular process that degrades damaged proteins and mitochondria. The failure of this process in the elderly to effectively rid the body of such damaged proteins and organelles leads to the age-associated malfunctions of many biological processes.

Mitochondria is an intracellular signaling organelle that communicates with the rest of the body to regulate metabolism and cell fate and thus, manipulation of mitochondria is believed to be involved in addressing a majority of age related diseases. Mitochondria have their own small collection of genes, which were once thought to play only minor roles within cells but now appear to have important functions throughout the body. Humanin and MOTS-c, hormones that appear to have significant roles in metabolism and diseases of aging, are unlike most other proteins, as they are encoded in mitochondria, rather than in the cell's nucleus where most genes are contained. Aged mammals contain high quantities of oxidized lipids and proteins, as well as damaged/mutated DNA, particularly in the mitochondrial genome. A major effect of mitochondrial dysfunction is an inappropriately high generation of ROS and proton leakage, resulting in lowering of ATP production in relation to electron input from metabolism. Leaked ROS and protons cause damage to a wide range of macromolecules, including enzymes, nucleic acids and membrane lipids within and beyond mitochondria and thus are consistent with the inflammation theory of aging as being proximal events triggering the production of pro-inflammatory cytokines. Free radicals can damage the mitochondrial inner membrane, creating a positive feedback-loop for increased free-radical creation. Induction of ROS generates mtDNA mutations, in turn leading to a defective respiratory chain. Defective respiratory chain generates even more ROS and generates a vicious cycle. One aspect of the present invention is directed to a therapeutic approach that employs autophagy, and preferably mitophagy, to reduce muscle damage and wasting. Thus, in certain embodiments, the use of the described treatment can be employed to combat human muscular dystrophy (DMD). Autophagy is known to be defective in human muscular dystrophy and such defect contributes to the pathogenesis of the disease.

Mitochondria are the cell's chief energy producing organelles. A cell can contain hundreds of mitochondria, the DNA of which encodes a subset of mitochondrial RNA and proteins. The mitochondrial theory of aging proposes that mutations progressively accumulate within the mitochondrial DNA. The consequences are predicted to be particularly dire for non-proliferative cells in organs that have a minimal capacity to regenerate (quiescent tissues), such as the heart and brain. The activity of master regulators of mitochondrial function and number diminishes with ageing, further contributing to mitochondrial deficiency. For example, with age, telomere damage in the nucleus triggers the activation of p53, which can have different effects. p53 is a gene that directs damaged cells to stop reproducing or die. The gene helps prevent cancer in younger people, but may be partly responsible for aging by impairing the body's ability to renew deteriorating tissues. Prominent age related diseases are further believed to be related to hormesis, in which biological stress, such as exercise, elicits a biological response that confers resistance to greater amounts of stress. This effect is due to increased formation of free radicals within the mitochondria causing a secondary induction of increased antioxidant defense capacity. Mitochondria are central to metabolic processes and are is involved energy production, programmed cell death, reactive oxygen species (ROS) generation, and is implicated in various stages of major diseases including cancer, diabetes, neurodegenerative diseases, and aging. In proliferative cells, p53 halts both cell growth and DNA replication, potentially causing apoptotic cell death. p53 also represses the expression of PGC-1 in mitochondria, reducing the function and number of these organelles, and so leading to age-related dysfunction of mitochondrion-rich, quiescent tissues. The mitochondrial derangements driven by loss of PGC-1 activity may independently lower the threshold for the generation of toxic intermediates such as reactive oxygen species (ROS), which damage mitochondrial DNA, thus setting up a vicious cycle of further mitochondrial dysfunction. Mitochondria-derived humanin shares 92-95% identity with several nuclear-encoded cDNAs. A 24 amino acid peptide, known as humanin (HN), is highly conserved among species (between 90-100% homology), including lower organisms. Unlike most other proteins, humanin and MOTS-c are encoded in mitochondria, the structure within cells that produces energy from food, instead of in the cell's nucleus where most genes are contained. As humanin and MOTS-c are hormones that have significant roles in metabolism and the diseases of aging, the regulation of the same via production of the same via an individual's microbiome forms one aspect of various embodiments of the present invention. Similarly, the SHLP family of compounds that are expressed by mitochondria play a major role in the intracellular signaling and communication to regulate metabolism and cell fate and thus are important in addressing methods for combating aging.

MOTS3 is a non-toxic natural peptide derived from the mitochondria that has a general metabolic regulatory role. It is the first of its kind that provides strong body weight and blood glucose regulation as well as activation of AMPK, which is a major drug target for diabetes and cancer via the mTOR pathway. It is from an entirely novel category of drugs, i.e. mtDNA-derived signaling peptides. In various embodiments of the present invention, MOTS3 is used to treat various age-related disease with metabolic implications such as cancer.

Polyphenolic compounds have a profound effect on mitochondrial structure and function. Curcumin, a well-known polyphenolic compound, is an abundant component of turmeric. Curcumin improves mitochondrial dynamics regarding mitochondrial biogenesis and mitophagy. In addition to curcumin, other natural compounds can be employed by splicing in genes using CRISPR-Cas systems to achieve the therapeutically effective dosages of such natural compounds to target particular pathways, including tomatidine, p53, diallyl trisulfide, resveratrol, apigenin, cyclopamine, and sulforaphane. These natural compounds can induce cancer signaling pathway manipulation. The mechanisms of action of different phytochemicals against inflammation processes and prevention of chronic noncommunicable diseases (e.g., obesity, diabetes, coronary heart disease, and hypertension) is therefore a central theme of various embodiments of the present invention, with the employment of an individual's microbiome being the preferred way in which such compounds are administered.

Aging is associated with a decline in mitochondrial function and the accumulation of abnormal mitochondria. Altered expression of some mitochondrial dynamics proteins is associated with aging and with age-related alterations in humans. The dysregulation of mitochondrial dynamics leads to age-induced accumulation of unhealthy mitochondria. Cell senescence is increasingly recognized as a major contributor to the loss of health and fitness associated with aging. Senescent cells accumulate dysfunctional mitochondria; oxidative phosphorylation efficiency is decreased and reactive oxygen species production is increased. The turnover of mitochondria (a term referred to as mitophagy) is perturbed in senescence contributing to mitochondrial accumulation. The maintenance of an adequate pool of functional mitochondria is crucial for tissue homeostasis. Through their bacterial ancestry, molecules produced by mitochondria contribute to mounting an inflammatory response by interacting with receptors similar to those involved in pathogen-associated responses and are involved in conditions associated with inflammation, aging and various degenerative diseases. Mitochondria are deeply involved in the aging process mainly through respiratory dysfunction and oxidant generation and participate in various functions, including heme metabolism, regulation of intracellular calcium homeostasis, modulation of cell proliferation, and integration of apoptotic signaling. Together with mitochondrial dysfunction, chronic inflammation is another hallmark of both aging and degenerative diseases. The two phenomena are related to one another in that circulating cell-free mitochondrial DNA (mtDNA) is a functional link between mitochondrial damage and systemic inflammation. Sarcopenia, the loss of skeletal muscle mass and strength in the aged, is an important medical condition but its etiology is incompletely understood. Because autophagy promotes myofiber atrophy in the young, it was believed that autophagy inhibition would prevent sarcopenia. However, autophagy has been observed to actually maintain muscle mass and its function declines during muscle aging. Basal autophagy protects from age-related muscle dysfunction by promoting the selective degradation of misfolded proteins and dysfunctional organelles. Conversely, it has been observed that autophagy inhibition leads to loss of muscle strength and induces a maladaptive stress response responsible for myofiber atrophy in the aged. Muscle autophagy and associated signaling pathways induce systemic responses in other aging tissues by modulating the expression and secretion of myokines. Selective autophagy may prevent sarcopenia, delay systemic aging, and extend the health span of humans. In various embodiments of the present invention, tomatidine produced by one's microbiome addresses the maintenance of muscle health while not interfering with selective autophagy, thus assisting in delaying aging.

Mammalian mitochondria are organelles that produce more than 90% of cellular ATP under aerobic conditions through a process called oxidative phosphorylation. Mitochondria are also the site for redox reactions that are necessary to maintain oxidative phosphorylation, and is the site of production of reactive oxygen species (ROS), which in controlled production have a signaling function, but in overproduction are toxic and believed to be the cause of many human diseases, as well as aging. Mitochondria play a central role in bioenergetics and metabolism. One hypothesis to explain aging is the free radical theory, which proposes that cells, organs, and organisms age because they accumulate reactive oxygen species (ROS) damage over time. Mitochondria play a central role as the principle source of intracellular ROS. Muscle mass and muscle strength begin to decline around the fourth decade, and this decline is accelerated with advancing age. Excessive ROS formation causes detrimental effects on proteins and lipids, which induces cellular dysfunction and ultimately cell death. The amount of ROS increases with aging and contributes to damage of the DNA and to oxidative modifications of proteins and lipids. Defects in mitochondrial dynamics are linked to senescence. Mitochondria have emerged as central regulators of the ageing process. Mitochondrial function in aged skeletal muscle and aged myocardium is impaired at various levels including ROS formation.

Exercise, restriction of calories, and addressing hormone signaling can all result in an extension of a human's healthspan. But these have proven difficult for individuals to implement consistently. While not bound by theory, the present inventors contend that the shortening of telomeres and the employment of enzymes involved in rebuilding telomeres resulting in the lengthening of telomeres at the risk of cancer is due to the effects of such enzymes on the mutation of p53, thus generating an oncogenic response and depriving the individual of the cancer-inhibitory actions of wild-type p53. Various aspects of the present invention are directed to the use of statins to ameliorate the mutated oncogenic characteristics of mutant p53, with the concomitant expression, via an individual's microbiome, of competently folded and cancer suppressing p53. Senescent cells secrete a host of molecules that, in young people, stimulate regeneration and repair. But over time, as more and more cells turn senescent, levels of these secreted molecules stop positively influencing their neighbors and begin causing inflammation. Groups of senescent cells produce such high levels of these chemicals that other, normal cells are persuaded to turn senescent. While senescent cells help protect us from cancer, their accumulation in old age is also problematic. Thus, destruction of senescent cells in humans that are old may be beneficial, or at least finding ways to reduce the amount of undesired chemicals generated from such cells is one objective in the battle against aging. Reprogramming senescent cells is believed to be an alternative and perhaps better way to address aging, as mice experiments have shown that by temporarily activating four genes known to make stem cells pluripotent, aging is halted with signs of rejuvenated muscle, pancreas, and spleen tissue, as well as more youthful skin, in addition to increase lifespan. One aspect of the present invention is directed to achieving cellular rejuvenation by modifying microbes such that an individual's own microbiome generates desired combinations of chemicals that extend life and health spans, without the need to alter human genes.

Metformin is known to decrease liver glucose production and boost insulin sensitivity. It has been observed that people with type 2 diabetes taking metformin lived longer than did a control group of similar people without diabetes, who therefore didn't take the drug. Thus, people lived longer with diabetes than without it, as long as they were taking metformin, indicating that metformin protects against a basic aging process. Providing effective amounts of metformin via the production of the same by the microbiome of an individual is part of various embodiments of the present invention.

Mitochondria are dynamic double-membrane bound organelles which have key roles in a variety of cellular functions. Recent evidence shows the promising role of polyphenolic compounds on mitochondrial structure and function. Curcumin, a well-known polyphenolic compound, is an abundant component of turmeric. The promising roles of curcumin against different diseases are highly publicized.

Resveratrol (3,4',5-trihydroxystilbene; $C_{14}H_{12}O_3$) is a polyphenolic phytoalexin found in grapes, berries, peanuts, and wines. Resveratrol has been viewed as an antioxidant, anti-inflammatory, anti-apoptotic, and anticancer agent. Moreover, it has been reported that resveratrol modulates mitochondrial function, redox biology, and dynamics in both in vitro and in vivo experimental models. Resveratrol also attenuates mitochondrial impairment induced by certain stressors. Resveratrol upregulates, for example, mitochondria-located antioxidant enzymes, decreasing the production of reactive species by these organelles. Resveratrol also triggers mitochondrial biogenesis, ameliorating the mitochondria-related bioenergetics status in mammalian cells. Brain cells (both neuronal and glial) are susceptible to mitochondrial dysfunction due to their high demand for adenosine triphosphate (ATP). Additionally, brain cells consume oxygen ($O_2$) at very high rates, leading to a proportionally high mitochondrial production of reactive species. Therefore, strategies focusing on the maintenance of mitochondrial function in these cell types are of pharmacological interest in the case of neurodegenerative diseases, which involve mitochondrial impairment and increased generation of reactive species, leading to neuroinflammation and cell death. The mechanism by which resveratrol protects mitochondrial function and dynamics is not completely understood, and further research would be necessary in order to investigate exactly how resveratrol affects mitochondria-related parameters. Furthermore, it is particularly important because resveratrol is able to induce cytotoxicity depending on its dosage.

In certain embodiments, the production of therapeutically effective amounts of resveratrol by an individual's microbiome is employed to address delaying and/or treating aging, as well as cancer. Resveratrol is a polyphenolic antioxidant that activates mitochondrial Sirt3, which results in mitophagy. While not bound by theory, it is believed that resveratrol modifies the intracellular environment by changing the oxidizing milieu into a reducing milieu and upregulating intracellular glutathione, potentiates a signal transduction cascade consisting of Sirt1/Sirt3-Foxo3a-PINK1-PARKIN-mitochondrial fusion fission-mitophagy and that leads to an anti-aging environment.

Aging is a major international concern that brings formidable socioeconomic and healthcare challenges. Tomatidine extends lifespan and healthspan in C. elegans, an animal model of aging which shares many major longevity pathways with mammals. Tomatidine improves many C. elegans behaviors related to healthspan and muscle health. Tomatidine maintains mitochondrial homeostasis by modulating mitochondrial biogenesis and PINK-1/DCT-1-dependent mitophagy. Mechanistically, tomatidine induces mitochondrial hormesis by mildly inducing ROS production, which in turn activates the SKN-1/Nrf2 pathway and possibly other cellular antioxidant response pathways, followed by increased mitophagy. Tomatidine-treated C. elegans exhibited increased levels of many free amino acids (leucine, threonine, isoleucine, tryptophan, proline, arginine, histidine, valine, methionine) suggesting an increased catabolism. Collectively, these results demonstrate that tomatidine affects several metabolic pathways which may be integral to its anti-aging properties.

Aging is becoming an international challenge to healthcare systems in both developed and developing countries. Research regarding mitochondrial dysfunction and age-related diseases, such as neurodegenerative diseases, have highlighted the importance of mitochondrial homeostasis for healthy aging and disease resistance. Mitochondrial homeostasis relies on mitochondrial biogenesis and by selective removal of dysfunctional or damaged mitochondria by mitochondrial autophagy (mitophagy). Impaired mitophagy occurs in physiological aging.

Gene expression analysis reveals regulation of the mitochondrial pathway by tomatidine. Tomatidine has significant effects on mitochondria function, as evidenced by changes in several mitochondria-related signaling pathways, including those affecting the electron transport chain, the mitochondrial inner membrane space and matrix, and the metabolism of glutathione. Additionally, tomatidine affects mitochondrial function and ROS metabolism.

Compromised mitochondrial quality and function contributes to biological and pathological aging, and many major aging-related diseases. Accumulation of damaged mitochondria within cells can trigger apoptosis, inflammation, and cell senescence. Sarcopenia is a common aging phenotype for which there is no effective therapy, affecting 13-24% of people over 60 years old and increasing to more than 50% in people over 80 years old. Tomatidine preserves muscle function during aging, and extends lifespan. Tomatidine improves mitophagy in both C. elegans and cultured human cells that lack bacteria. Tomatidine may protect muscle function from age-related deterioration by activating the Nrf2/SKN-1-DCT-1 pathway and up-regulating mitophagy and antioxidant cellular defenses. Tomatidine stimulates the growth of mouse skeletal muscle cells, in part by activating the mTOR pathway. In humans, sarcopenia is a common feature of aging that involves the accumulation of dysfunctional mitochondria and associated deterioration of muscle fiber cells themselves, in combination with infiltration of adipocytes and inflammatory immune cells. In addition, an impaired ability of muscle stem cells to generate new myocytes may be impaired with aging and more so in sarcopenia.

Emerging evidence suggests a pivotal role of mitophagy in health and aging, pointing to the fact that mitophagy induction can improve healthspan and lifespan. Mitophagy is required for tomatidine-induced extension of healthspan and stress resistance. There is a signaling role for ROS in the stimulation of mitophagy in cells under mild stress. Moderately elevated ROS levels can induce mitophagy, which then clears aged or dysfunctional mitochondria. However, if mitophagy is compromised and/or ROS levels are excessively high, mitochondrial dysfunction becomes exacerbated in a vicious cycle. While excessive ROS can cause cellular and systemic damage and promote disease, moderately elevated ROS levels enhance cellular stress resistance and protect against disease. Tomatidine can induce a moderate increase in ROS levels which is necessary to trigger mitophagy.

Many of the chemicals produced in vegetables, fruits and other plants (phytochemicals) that have been found to have beneficial effects on cells and organisms are believed to function as noxious agents that dissuade insects and other organisms from consuming the plants. Herbivorous organisms evolved multiple mechanisms to prevent consumption of toxic amounts of the phytochemicals. Such noxious phytochemicals are typically concentrated in the parts of plants that are exposed to the environment and/or are involved in seed production including the 'skin' of fruits, and developing buds/sprouts. In the case of the tomato fruit, tomatidine is present in high amounts in the unripe green tomato and in much lower amounts in the ripe red tomato. This is consistent with a role for tomatidine in protecting the unripe tomato against consumption, with the reduction in tomatidine levels in the ripe fruit then enabling consumption of the fruit and dispersal of the seeds by the consumer. Moderate amounts of tomatidine can activate adaptive cellular stress responses in muscle cells and thus, counteract age-related dysfunction and degeneration. One prominent response of cells to tomatidine is induction of mitophagy, which preserves cellular function during aging. Mitochondrial dysfunction and defective mitophagy are implicated in the etiology of several major age-related diseases. Certain aspects of the present invention are directed to alterations of an individual's microbiota in terms of the particular composition, diversity and functional features of the intestinal microbiota to combat chronic inflammation and various aging-associated pathologies. Such modification of an individual's microbiome, whether it be skin, oral, vaginal, but especially intestinal gut microbiota, is performed in a manner to favorably enhance antioxidant activity, improve immune homeostasis, suppress chronic inflammation, and regulate fat metabolism.

To comply with written description and enablement requirements, all references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. Incorporated herein by this reference are the following US patent publications: 20170079947 to Richards; 20140296139 to Cohen et al.; 20160175327 to Adams et. al.; 20100081681 to Blagosklonny and 20120283269 to Blagosklonny; U.S. Patent Publication Nos. 20140030332 to Baron, et al., 20070123448 to Kaplan et al.; 20160000841 to Yamamoto, et al.; 20160095316 to Goodman et al.; 20160158294 to Von Maltzahn; 20140294915 to Kovarik; U.S. Pat. No. 8,034,601 to Boileau et al.; 20130225440 to Freidman, et al., 20150071957 to Kelly et al., 20160151428 to Bryann et al.; 20160199424 to Berry et al.; 20160069921 to Holmes, et al.; 20160000754 to Stamets; U.S. Pat. No. 9,044,420 to Dubensky, Jr, et al.; 20160120915 to Blaser et. al.; 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 2015/0132263 to Liu; and 2014/0068797 to Doudna; 2014/0255351 to Berstad et al.; 2015/0086581 to Li; PCT/US2014/036849 and WO 2013026000 to Bryann; U.S. Pat. Publication No. 2015/0190435 to Henn; 2012/0142548 to Corsi et al.; U.S. Pat. Nos. 6,287,610, 6,569,474, U.S. 2002/0009520, U.S. 2003/0206995, U.S. 2007/0054008; and U.S. Pat. No. 8,349,313 to Smith; U.S. Pat. No. 9,011,834 to McKenzie; 20150004130 to Faber et. al, 20160206666 to Falb; 20160206668 to Kort et. al; and WO2015069682A2 to Asesvelt, et. al.; 20160199424 to Berry et al.; 20130326645 to Cost et al.; 2012/0276149 to Littman; and U.S. Pat. No. 9,314,489 to Kelly et. al.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention. It is important, therefore, that the claims be regarded as including any such equivalent construction insofar as they do not depart from the spirit and scope of the present invention.

What is claimed is:

1. A method of treating bladder cancer in a subject in need of such treatment, said method comprising administering to a gut microbiome of a subject with bladder cancer an effective amount of a bacterial composition comprising *bacillus calmette-guerin*, said bacterial composition comprising bacteria adapted to produce p53.

2. The method of claim 1, wherein the bacterial composition comprises bacteria modified via a clustered regularly interspaced short palindromic repeats (CRISPR) CRISPR associated protein (Cas) system using a CRISPR-Cas system to express p53.

3. The method of claim 1, wherein the bladder cancer is a metastatic cancer.

4. A method of claim 1, wherein said bacterial composition further includes a microbe selected from the group consisting of *Streptococcus, Veillonella, Fusobacterium* and *Treponema*.

5. The method as set forth in claim 4, further comprising administering to the subject at least 0.1 mg of rapamycin.

6. The method of claim 1, wherein a bacterium in the bacterial composition has been modified via a CRISPR-Cas system to express p53.

7. The method of claim 1, wherein the bacterial composition further comprises a bacterium selected from the group consisting of *Chlamydia, Shigella flexneri, Mycoplasma bacteria*, and *H. pylori*.

8. The method of claim 1, wherein the bacterial composition comprises *H. pylori* bacteria.

9. A method of treating bladder cancer in a subject in need of such treatment, said method comprising administering to a gut microbiome of a subject with bladder cancer an effective amount of a bacterial composition comprising a bacteria that has been modified to express a therapeutically effective amount of p53, said bacterial composition including bacteria selected from the group consisting of *Streptococcus, Veillonella, Fusobacterium* and *Treponema*.

10. A method of treating bladder cancer in a subject in need of such treatment, said method comprising administering to a gut microbiome of a subject with bladder cancer a bacterial composition comprising a therapeutically effective amount of *bacillus calmette-guerin* bacteria, wherein the *bacillus calmette-guerin* bacteria has been modified using a CRISPR-Cas system to produce p53.

11. The method of claim 10, wherein the bacterial composition comprises *Veillonella* bacteria.

12. The method of claim 10, wherein the bacterial composition comprises *Streptococcus*.

13. The method of claim 10, wherein said bacterial composition comprises butyrate producing bacteria.

14. The method of claim 10, wherein the bacterial composition comprises *Fusobacterium* and *Treponema*.

* * * * *